(12) United States Patent
Patel et al.

(10) Patent No.: US 12,133,845 B2
(45) Date of Patent: Nov. 5, 2024

(54) OROMUCOSAL SOLUTIONS OF ZOLPIDEM OR PHARMACEUTICALLY ACCEPTABLE SALTS THEREOF

(71) Applicant: TROIKAA PHARMACEUTICALS LIMITED, Ahmedabad (IN)

(72) Inventors: Nisheel K. Patel, Ahmedabad (IN); Ketan R. Patel, Ahmedabad (IN); Milan R. Patel, Ahmedabad (IN); Kush M. Patel, Ahmedabad (IN); Asheel K. Patel, Ahmedabad (IN)

(73) Assignee: TROIKAA PHARMACEUTICALS LIMITED, Ahmedabad (IN)

( * ) Notice: Subject to any disclaimer, the term of this patent is extended or adjusted under 35 U.S.C. 154(b) by 597 days.

(21) Appl. No.: 17/283,328

(22) PCT Filed: Oct. 4, 2019

(86) PCT No.: PCT/IN2019/050734
§ 371 (c)(1),
(2) Date: Apr. 7, 2021

(87) PCT Pub. No.: WO2020/075183
PCT Pub. Date: Apr. 16, 2020

(65) Prior Publication Data
US 2022/0000845 A1 Jan. 6, 2022

(30) Foreign Application Priority Data
Oct. 8, 2018 (IN) .............................. 201821038060

(51) Int. Cl.
| | | |
|---|---|---|
| A61K 31/437 | (2006.01) | |
| A61K 9/08 | (2006.01) | |
| A61K 47/02 | (2006.01) | |
| A61K 47/10 | (2017.01) | |
| A61K 47/14 | (2017.01) | |
| A61K 47/26 | (2006.01) | |
| A61K 47/32 | (2006.01) | |
| A61K 47/40 | (2006.01) | |

(52) U.S. Cl.
CPC .............. *A61K 31/437* (2013.01); *A61K 9/08* (2013.01); *A61K 47/02* (2013.01); *A61K 47/10* (2013.01); *A61K 47/14* (2013.01); *A61K 47/26* (2013.01); *A61K 47/32* (2013.01); *A61K 47/40* (2013.01)

(58) Field of Classification Search
CPC ........ A61K 31/437; A61K 9/08; A61K 47/02; A61K 47/10; A61K 47/14; A61K 47/26; A61K 47/32; A61K 47/40; A61K 9/006; A61K 47/38; A61P 25/20
See application file for complete search history.

(56) References Cited

U.S. PATENT DOCUMENTS

2011/0280916 A1* 11/2011 Blondino ................. A61K 9/08
514/226.5

FOREIGN PATENT DOCUMENTS

| WO | WO-9946417 A1 | 9/1999 |
| WO | WO-2005032519 A1 | 4/2005 |
| WO | WO-2005079761 A1 | 9/2005 |
| WO | WO-200712395 A1 | 2/2007 |
| WO | WO-2008141264 A1 | 11/2008 |

OTHER PUBLICATIONS

International Search Report and Written Opinion of the International Searching Authority, issued in PCT/IN2019/050734, mailed Jan. 21, 2020; ISA/EP.

* cited by examiner

*Primary Examiner* — Eric Olson
*Assistant Examiner* — Samuel L Galster
(74) *Attorney, Agent, or Firm* — Baker Hostetler

(57) ABSTRACT

The present invention relates to buccal or sublingual formulations of Zolpidem or pharmaceutically acceptable salt thereof. The formulations minimize the amount of penetration enhancers and yet provide rapid transmucosal penetration of the drug. These formulations not only provide desired a concentration (0.5% to 10% w/v) of the drug in the form of clear solution, but also achieve stable formulations throughout the shelf-life of at least about 2 years. The pH of the stable non-aqueous solutions of the present invention is in the range of range of 5 to 9, preferably 6 to 9 more preferably 7 to 9.

13 Claims, No Drawings

OROMUCOSAL SOLUTIONS OF ZOLPIDEM OR PHARMACEUTICALLY ACCEPTABLE SALTS THEREOF

CROSS-REFERENCE TO RELATED APPLICATIONS

This application is a 371 U.S. National Stage of International Application No. PCT/IN2019/050734, filed on Oct. 4, 2019, which claims priority to Indian application No. 201821038060, filed on Oct. 8, 2018. The entire disclosures of the above applications are incorporated herein by reference.

FIELD OF THE INVENTION

The present invention relates to a stable, non-aqueous solutions of Zolpidem or pharmaceutically acceptable salt(s) thereof. The solutions of the present invention are suitable for administration via oromucosal route. More particularly, the present invention relates to stable, non-aqueous solutions of Zolpidem or pharmaceutically acceptable salt(s) that provide rapid onset of action when administered into the oral cavity via buccal, sublingual or oromucosal route, wherein the pH of the formulation is in the range of 5 to 9.

BACKGROUND OF THE INVENTION

Sleep has an important role in the regulation of the central nervous system (CNS), and the body's physiological functions including regulating metabolism, catabolism, temperature, learning and memory consolidation. Insomnia is a sleep disorder characterized by one or more of the following traits: difficulty falling asleep (e.g., sleep onset latency (SOL) of more than 30 minutes), insufficient sleep (e.g., total sleep time (TST) of less that 5.5-6 hours), numerous nocturnal awakenings, early morning awakenings with the inability to resume sleep, or non-restorative sleep.

Insomnia is more prevalent in women, older adults, shift workers and patients with medical and psychiatric illness. Difficulties of sleep initiation are more common in young adults while problems of maintaining sleep are more common in middle-aged and older adults. Because of its high incidence, and because its symptoms are usually mild and transient, the importance of insomnia is frequently underestimated. However, as a chronic disorder affecting about 10% of the population, its treatment is often challenging and associated with a substantial number of co-morbid symptoms (i.e., depression, anxiety).

The treatment of insomnia has two primary objectives. These objectives include improving quality or quantity of sleep and improving daytime impairments.

Initial approaches of treatment usually include at least one behavioral intervention, such as stimulus control therapy or relaxation therapy. The medication for the treatment of insomnia includes benzodiazepines (BZD), non-benzodiazepines, Melatonin-agonist, Tricyclic antidepressant, barbiturates, etc.

Zolpidem and BDZs share the property of binding to a subunits (the "BDZ receptor") of the $GABA_A$ receptor/chloride channel complex. However, there is a decisive difference in selectivity concerning the subtypes. For example, BDZs are relatively non-selective in this regard causing anti-excitatory hyper-polarizations in many places in the CNS. These actions lead to more generalized neuronal inhibitions and numerous effects exceeding sedation and sleep promotion, such as anxiolytic, anticonvulsant and relaxant actions.

Zolpidem Tartrate is chemically, N, N, 6-trimethyl-2-p-tolylimidazo [1,2-a] pyridine-3-acetamide L-(+)-tartrate (2:1) and exhibits strong hypnotic and sedative actions with negligible anxiolytic, muscle relaxing, or anticonvulsant properties. Zolpidem Tartrate is widely prescribed for the short-term treatment of insomnia. It is relatively well-tolerated and almost devoid of the side effects typically associated with BDZs.

Attempts have been made to provide Zolpidem or its salt in solid oral dosage forms such as tablets. Due to absence of water, these dosage forms are relatively more stable. A stable liquid formulation will not only be in the form of a clear solution but also will remain clear, without precipitation of the drug, on storage.

The drug is administered in solid form, and therefore it is possible to deliver higher amount of drug through these solid dosage forms. Accordingly Ambien® and Ambien® CR tablets (Sanofi Aventis, USA) provides 10 and 12.5 mg drug per tablet respectively.

The issue with solid dosage form is that it needs to get disintegrated and dissolved before the drug therein can be transported into the system, and therefore the onset of action for these solid dosage forms will be much slower compared to the liquid dosage forms, wherein the drug is readily available in solution for penetration across mucosa. Another drawback of these tablet formulations is daytime drowsiness which affects the quality of life of the patient.

WO9916417 (WO'417) discloses buccal spray composition for transmucosal administration of a pharmacologically active compound selected from a group including sleep inducers. WO'417 discloses two-type of formulations. The buccal polar composition comprises formulation (I): aqueous polar solvent 30-99.89%, active compound 0.001-60%, optionally containing flavoring agent 0.1-10%. The non-polar composition of the invention comprises formulation (II): non-polar solvent 20-85%, active compound 0.005-50% and optionally flavoring agent 0.1-10% and propellant 50-80%. The specification does not disclose any specific formulation of Zolpidem or its salts. It is to be noted that the propellant-free formulations disclosed in WO'417 contain substantial quantity of water. The presence of water would substantially reduce the shelf-life of the formulations and hence it is desirable to prepare formulations without water.

WO2005079761 (WO'761) and WO2006128022 (WO'022) disclose oral solid compositions for the delivery of a hypnotic agent across oral mucosa. It is to be noted that WO'761 provides about 1.0 to about 5.5 weight percent zolpidem in a solid dosage form which, takes a long time to get absorbed. WO'761 and WO'022, fail to achieve the drug concentration of 0.5% to 10% w/v in a solution formulation, wherein the drug is ready for absorption.

WO2006046041 (WO'041) discloses fast acting solid dose formulations of Zolpidem in the form of mucoadhesive tablets suitable for transmucosal administration. The invention in this PCT Publication which is in a solid dosage form remains in constant contact with the oral mucosa which causes considerable discomfort to the patient.

WO2005032519 (WO'519) discloses buccal aerosol sprays or capsules using a polar and non-polar solvent, which provide Zolpidem for rapid absorption through oral mucosa, resulting in fast onset of action. The buccal polar compositions of the invention comprise formulation aqueous polar solvent, zolpidem, and optional flavoring agent; formulation II: aqueous polar solvent, zolpidem, optionally flavoring agent, and propellant; formulation III: non-polar solvent, zolpidem, and optional flavoring agent; formulation IV: non-polar solvent, zolpidem, optional flavoring agent, and propellant; formulation V: a mixture of a polar solvent and a non-polar solvent, zolpidem, and optional flavoring agent; formulation VI: a mixture of a polar solvent and a non-polar solvent, zolpidem, optional flavoring agent, and propellant.

The "propellant-free" buccal spray of Zolpidem in WO'519 uses a polar and/or non-polar solvent to quickly deliver Zolpidem or a pharmaceutically acceptable salt thereof in an amount between 0.01 to 20% (w/w) of the total formulation.

Despite using a solvent system containing the polar solvents in very high proportion (of propylene glycol and ethanol 30 and 99%) in formulation of in WO'519, it was not possible to solubilise the drug completely, thereby producing hazy solutions. Further very high proportion of alcohol, which also acts as a penetration enhancer, leads to unpleasant sensation in the oral cavity. WO'519 does not disclose the pH of the formulations. When measured by the present inventors, the pH was ~5. The liquid formulation of Zolpidem (Zolpimist®) marketed by Novadel Pharma US (the applicant of WO'519), has a pH of 3 to 4 at which the drug remains solubilized indicating that the invention is workable only in the pH range<5.

The invention disclosed in WO'519 teaches that 8% of citrate buffer is crucial for solubilisation of the drug in propellant-free formulation containing 2.5 w/w Zolpidem and a polar solvent comprising 15% Propylene glycol and ~64% ethanol maintained at pH of <5. When the pH of these solutions is increased to 5 and above, a hazy solution is formed. Further, water in fairly high proportions is used as an essential ingredient. WO'519 fails to provide liquid formulations that are stable on storage. The invention disclosed in WO'519 also teaches "propellant-free" formulations prepared using oily components and lemon oil wherein the drug concentration achieved is only 0.5%. The pH of this formulation is also less than 5. It has been found that such formulations are not workable for drug concentrations of 2.5% w/v.

WO2007123955 (WO'955) discloses stable hydro-alcoholic formulations of an active pharmaceutical agent suitable for oral spray administration. WO'955 uses water as an essential component of the solvent system for the propellant-free buccal formulations. The pH for these formulations is maintained in the range of 7 to 12 to deliver a variety of active pharmaceutical ingredients in aqueous formulations. However, it has been found that it is not possible to prepare a clear solution of Zolpidem Tartrate using the solvent system disclosed in WO'955 in the pH range of 7 to 12.

WO2008141264 (WO'264) discloses oral sprays formulations for transmucosal absorption of Zolpidem using a combination of polar and non-polar solvents. These formulations may optionally use propellants. The formulations covered in this reference are available in the market under the brand name Zolpimist®.

Typically, WO'264 discloses oral spray formulations comprising 0.05-10% Zolpidem or a pharmaceutically acceptable salt thereof; a polar or non-polar solvent or mixture thereof. These formulations may further comprise 0-1% taste mask and/or flavoring agents; and 0-1% preservative; and a propellant. All the exemplified formulations of Zolpidem contain water. All the exemplified formulations disclosed in WO'264 have a pH of 3-4. The present inventors have found that when the pH of these formulations are increased to about 5, the drug precipitates as curdy white mass demonstrating that these formulations are not suitable for oromucosal administration. Further the present inventors have found that the transmucosal penetrations of the formulations disclosed in WO'264 has $T_{max}$ of 20 minutes.

The prior art disclosing inventions to improve transmucosal penetration of Zolpidem by providing a liquid dosage form with or without propellants has the following limitations:

They fail to provide a desired drug concentration (0.5% to 10% w/v) in the form of a clear solution with the desired shelflife of at least about 2 years. Hence, most formulations available in the market are in solid dosage forms.

They need water as an essential ingredient which results in lower stability of the drug, wherein the drug precipitates from the solution on storage.

They use very high proportion of penetration enhancers such as alcohol, in these formulations that lead to a possibility of side effects such as unpleasant sensation in the oral cavity.

They fail to achieve faster onset of action ($T_{max}$ of less than 20 minutes) by providing rapid transmucosal penetration of the drug over a pH range of 5 to 9. Hence the liquid formulations available in the market are maintained at pH less than 5.

To address the long-felt need of providing stable non-aqueous liquid formulations for effective transmucosal administration of Zolpidem or its pharmaceutically acceptable salts, the following technical issues with regard to such liquid dosage forms need to concurrently address:

1. Provide a concentration of 0.5% to 10% w/v of the drug in clear non-aqueous solutions;
2. Provide formulations that are stable for the entire shelf-life of at least two years over a broad pH range of 5 to 9; and
3. Minimize the amount of penetration enhancer(s) used in the formulation upto 30% v/v without compromising on the transmucosal penetration of the drug.
4. Provide rapid transmucosal penetration of the drug over a pH range of 5 to 9 thereby leading to faster onset of action.

Objects of the Invention

The main object of the present invention is to provide stable, non-aqueous solutions of Zolpidem or pharmaceutically acceptable salts thereof wherein the formulations provide rapid transmucosal penetration of the drug.

It is yet another object of the present invention to provide stable, non-aqueous solutions of Zolpidem or pharmaceutically acceptable salts thereof wherein the formulations provide 0.5 to 10% w/v, preferably 2.5% to 10% w/v, of Zolpidem or pharmaceutically acceptable salts thereof wherein pH of the formulation is in the range of 5 to 9, preferably in the range of 6 to 9, more preferably in the range of 7 to 9.

Another object of the present invention is to provide stable, non-aqueous formulations of Zolpidem or pharmaceutically acceptable salts thereof suitable for administration by buccal or sublingual or oromucosal route, wherein the formulations provide rapid onset of action due to rapid transmucosal penetration.

Another object of the present invention is to provide stable non-aqueous formulations of Zolpidem or pharmaceutically acceptable salts thereof, wherein rapid transmucosal penetration of the drug is achieved, by minimizing the amount of penetration enhancer(s) used in the formulation.

The present invention addresses the abovementioned and other needs by providing stable non-aqueous formulation of Zolpidem or its pharmaceutically acceptable salt by synergistic combination of components such as a judiciously selected solvent system, penetration enhancer(s) and other ingredients in a pH range of 5 to 9, preferably in the range of 6 to 9, more preferably in the range of 7 to 9. The formulations of the present invention surprisingly results in rapid transmucosal penetration as compared to the formulations known in the art.

DETAILED DESCRIPTION OF THE INVENTION

The present invention provides stable, non-aqueous solutions of Zolpidem or pharmaceutically acceptable salts thereof with rapid oromucosal absorption of the drug.

The challenge for the present inventors was to solubilise the desired concentration of Zolpidem or its pharmaceutically acceptable salts in non-aqueous liquid formulation and at the same time keeping it stable for the entire shelf life of the formulation.

The synergistic combination of the components of the present invention not only achieves stable non-aqueous liquid solutions of Zolpidem or its pharmaceutically acceptable salts, but it also maintains the drug in a solubilized state over a pH range of 5 to 9 for the entire shelf-life of at least 2 years.

Surprisingly, the solutions of the present invention achieve rapid transmucosal penetration of the drug as compared to the formulations disclosed in the prior-art. This leads to a faster onset of action when administered through sublingual route in animals. The present invention provides a solution with $T_{max}$<20 minutes. Most surprisingly, the present invention achieves the above mentioned advantages with minimized use of penetration enhancers in the solutions.

The solutions of the present invention comprises Zolpidem or pharmaceutically acceptable salts thereof, penetration enhancer(s), a non-aqueous solvent system, optionally pH adjusting agents and optionally a Polymer, wherein the pH of the solution is in the range of 5 to 9, preferably in the range of 6 to 9, more preferably in the range of 7 to 9.

The present invention provides a stable, non-aqueous solution of Zolpidem or its pharmaceutically acceptable salts wherein the concentration of Zolpidem or its pharmaceutically acceptable salts is in the range of 0.5 to 10% w/v of the solutions, preferably in the range of 2.5% to 10% w/v of the solutions.

The penetration enhancer(s) are selected from lower chain alcohol(s) with a carbon chain length of 1 to 5, preferably ethanol, isopropyl alcohol or mixtures thereof. The penetration enhancer(s) of the present formulation may also be selected from the lower chain alcohol(s), sodium glycocholate, sodium deoxycholate, sodium taurocholate, sodium glycodeoxycholate, sodium taurodeoxycholate, oleic acid, capric acid, lauric acid, lecithin, myristic acid, palmitic acid, lysophosphatidylcholine, phosphatidylcholine, azone, cyclodextrin, sodium lauryl sulphate, Polyoxyethylene-9-lauryl ether, Polyoxythylene-20-cetylether, Benzalkonium chloride, cetylpyridinium chloride, Vitamin E TPGS, Caprylocaproyl polyoxylglycerides, Stearoyl Macrogolglycerides, Propylene Glycol Dicaprylocaprate, Propylene Glycol Monocaprylate, Propylene Glycol monolaurate, N-Methyl-2-pyrrolidone or mixtures thereof.

In an embodiment, the solution comprises ethanol as penetration enhancer(s). The present invention attempts to minimize the proportion of penetration enhancer(s) to be incorporated in the solutions. The present invention comprises penetration enhancer(s) up to 30% v/v of the solutions, preferably in the range of 2 to 30% v/v of the solutions, more preferably in the range of 10 to 30% v/v of the solutions. In one of the embodiments, the present invention comprises less than 25% v/v of penetration enhancer(s), preferably in the range of 2 to 25% v/v of the solutions.

The non-aqueous solvent system of the present invention is selected from glycerol, propylene glycol, polyethylene glycol, propylene carbonate, glycofurol, isopropyl myristate, isopropyl palmitate, dimethyl sulfoxide, triethyl citrate, dimethylacetamide, benzyl alcohol, N-methyl-pyrrolidone, dimethyl isosorbide, ethyl acetate or combination thereof. Preferably, the present invention comprises the non-aqueous solvent system in a proportion of at least 40% v/v, preferably at least 50% v/v, more preferably at least 55% v/v of the formulation. In one of the embodiments the non-aqueous solvent system of the present invention is from 40% v/v to 99.5% v/v of the solutions.

The present invention provides solutions in the pH range of 5 to 9, preferably in the range of 6 to 9, more preferably in the range of 7 to 9. In order to adjust the pH of the solutions in the desired range, a pH adjusting agent known in the art may be included. The said agent may be selected from the pH adjusting compounds known in the art. The pH adjusting agent are preferably selected from meglumine, sodium bicarbonate, sodium carbonate, sodium hydroxide, triethanolamine, tromethamine, diethanolamine, monoethanolamine, sodium borate, sodium citrate dihydrate, calcium hydroxide, potassium bicarbonate, potassium citrate, potassium carbonate, tromethamine or combination thereof. The pH adjusting agent of the present invention are used in a quantity sufficient to adjust the pH of the formulation in the range of 5 to 9, preferably in the range of 6 to 9, more preferably in the range of 7 to 9.

The present invention may further comprise various auxiliary ingredients such as sweeteners, flavoring agents, taste masking agents etc known in the art. The flavoring agents of the present invention are selected from menthol, peppermint oil, maltol, ethyl maltol, ethyl vanillin, vanillin, spearmint, strawberry, cherry, raspberry, wintergreen, watermelon, grape flavors and their like. The sweeteners of the present invention are selected from neotame, sucrose, alitame, acesulfame potassium, aspartame, trehalose, xylitol, sucralose, sorbitol, saccharin sodium, neohesperidin dihydrochalcone, mannitol, maltitol, lactitol, fructose and their like.

In another embodiment, the formulation may further comprises a polymer such as polyvinylpyrrolidone, poly (vinyl pyrrolidone-co-vinyl acetate), polyvinylpolypyrrolidone, polymethacrylates, hydroxypropylmethyl cellulose, hydroxypropylmethylcellulose acetate succinate, hydroxyethyl cellulose, hydroxypropyl cellulose, hydroxypropyl betadex, polyvinyl alcohol, polyacrylic acid or combination thereof. The Polymer is incorporated in the range of up to 5% w/v of the solution. The Polymer, when used, is preferably incorporated in the range of 0 to 2% w/v of the solution or more preferably in the range of 1 to 2% w/v of the solution.

The present invention provides stable, non-aqueous solution of Zolpidem or pharmaceutically acceptable salt thereof that achieves rapid transmucosal absorption of the drug across the mucosa leading to fast onset of action.

Further, the present invention avoids the use of organic propellants and high proportion of penetration enhancer(s) which may lead to harmful side effects or discomfort in the mouth of the patient.

The present invention provides stable non-aqueous solutions suitable for administration through oromucosal route including buccal or sublingual route.

Non-limiting examples of the formulations of the present invention are provided below:

Formulation 1:

| Ingredients | Quantity in Percentage (%) |
| --- | --- |
| Zolpidem tartrate | 2.5% w/v |
| Meglumine | 1.4% w/v |
| Ethanol | 10% v/v |
| PVP K30 | 2% w/v |
| Neotame | 0.01% w/w |
| Glycerol | 25% v/v |
| Neohespiridine | 0.001% w/w |
| Propylene glycol | q.s to 100% |
| pH | 8 |

Formulation 2:

| Ingredients | Quantity in Percentage (%) |
| --- | --- |
| Zolpidem tartrate | 2.5% w/v |
| Meglumine | 1.4% w/v |
| Ethanol | 10% v/v |
| Neotame | 0.01% w/w |
| Glycerol | 25% v/v |
| Neohespiridine | 0.001% w/w |
| Propylene glycol | q.s to 100% |
| pH | 8.1 |

Comparative Formulation 3: (Zolpimist)

| Ingredients | Quantity in Percentage (%) |
| --- | --- |
| Zolpidem tartrate | 2.5% w/v |
| Propylene glycol | 18.73% w/w |
| Benzoic acid | 0.0265% w/v |
| Citric acid monohydrate | 5.12% w/v |
| (Citric acid Anhydrous) | (4.655% w/v) |
| Neotame | 0.0005% w/v |
| Hydrochloric acid | Qs to adjust the pH 3 to 4 |
| Flavoured fruit DC | 0.135% w/v |
| Purified water | q.s to 100% |

The pH of the formulation once prepared as per the formula was 3.5

Formulation 4:

| Ingredients | Quantity in Percentage (%) |
| --- | --- |
| Zolpidem tartrate | 1% w/v |
| Meglumine | 1.4% w/v |
| Ethanol | 5% v/v |
| PVP K30 | 2% w/v |
| Neotame | 0.01% w/w |
| Propylene glycol | q.s to 100% |
| pH | 7.5 |

Formulation 5:

| Ingredients | Quantity in Percentage (%) |
| --- | --- |
| Zolpidem tartrate | 5% |
| Meglumine | 2.8% w/v |
| Ethanol | 20% v/v |
| Neotame | 0.01% w/w |
| Propylene glycol | q.s to 100% |
| pH | 7.9 |

Formulation 6:

| Ingredients | Quantity in Percentage (%) |
| --- | --- |
| Zolpidem tartrate | 2.5% w/v |
| Meglumine | 1.4% w/v |
| Ethanol | 20% v/v |
| PVP K30 | 2% w/v |
| Neotame | 0.01% w/w |
| Propylene glycol | q.s to 100% |
| pH | 7.5 |

Formulation 7:

| Ingredients | Quantity in Percentage (%) |
| --- | --- |
| Zolpidem tartrate | 2.5% w/v |
| Meglumine | 1.4% w/v |
| Ethanol | 30% v/v |
| PVP K30 | 2% w/v |
| Neotame | 0.01% w/w |
| Propylene glycol | q.s to 100% |
| pH | 7.3 |

Formulation 8:

| Ingredients | Quantity in Percentage (%) |
| --- | --- |
| Zolpidem tartrate | 2.5% w/v |
| Meglumine | 1.4% w/v |
| Ethanol | 8% v/v |
| Cyclodextrin | 2% w/v |
| PVP K30 | 2% w/v |
| Glycerol | 25% v/v |
| Neotame | 0.01% w/w |
| Propylene glycol | q.s to 100% |
| pH | 7.6 |

Formulation 9:

| Ingredients | Quantity in Percentage (%) |
| --- | --- |
| Zolpidem tartrate | 2.5% w/v |
| Meglumine | 1.4% w/v |
| Ethanol | 8% v/v |
| Lecithin | 2% w/v |
| PVP K30 | 2% w/v |
| Glycerol | 25% v/v |
| Neotame | 0.01% w/w |
| Propylene glycol | q.s to 100% |
| pH | 7.8 |

Formulation 10:

| Ingredients | Quantity in Percentage (%) |
| --- | --- |
| Zolpidem tartrate | 2.5% w/v |
| Meglumine | 1% w/v |
| PVP K30 | 2% w/v |
| Ethanol | 10% v/v |
| Glycerol | 25% v/v |

-continued

| Ingredients | Quantity in Percentage (%) |
|---|---|
| Neotame | 0.01% w/w |
| Propylene glycol | q.s to 100% |
| pH | 6.2 |

Formulation 11:

| Ingredients | Quantity in Percentage (%) |
|---|---|
| Zolpidem tartrate | 2.5% w/v |
| Meglumine | 1.24% w/v |
| PVP K30 | 2% w/v |
| Ethanol | 10% v/v |
| Glycerol | 25% v/v |
| Neotame | 0.01% w/w |
| Propylene glycol | q.s to 100% |
| pH | 6.9 |

Formulation 12:

| Ingredients | Quantity in Percentage (%) |
|---|---|
| Zolpidem tartrate | 2.5% w/v |
| Meglumine | 1.8% w/v |
| PVP K30 | 2% w/v |
| Ethanol | 10% v/v |
| Glycerol | 25% v/v |
| Neotame | 0.01% w/w |
| Propylene glycol | q.s to 100% |
| pH | 8.6 |

Formulation 13:

| Ingredients | Quantity in Percentage (%) |
|---|---|
| Zolpidem tartrate | 2.5% w/v |
| Meglumine | 1.4% w/v |
| PVP K30 | 2% w/v |
| Ethanol | 10% v/v |
| DMSO | 50% v/v |
| Neotame | 0.01% w/w |
| Propylene glycol | q.s to 100% |
| pH | 9.0 |

Formulation 14:

| Ingredients | Quantity in Percentage (%) |
|---|---|
| Zolpidem tartrate | 2.5% w/v |
| Meglumine | 1.4% w/v |
| PVP K30 | 2% w/v |
| Ethanol | 10% v/v |
| PEG 400 | 34% v/v |
| Neotame | 0.01% w/w |
| Propylene glycol | q.s to 100% |
| pH | 8.2 |

Formulation 15:

| Ingredients | Quantity in Percentage (%) |
|---|---|
| Zolpidem tartrate | 2.5% w/v |
| Meglumine | 1.4% w/v |
| PVP K30 | 2% w/v |
| Ethanol | 10% v/v |
| Glycofurol | 38% v/v |

-continued

| Ingredients | Quantity in Percentage (%) |
|---|---|
| Neotame | 0.01% w/w |
| Propylene glycol | q.s to 100% |
| pH | 7.8 |

Formulation 16:

| Ingredients | Quantity in Percentage (%) |
|---|---|
| Zolpidem tartrate | 2.5% w/v |
| Meglumine | 1.4% w/v |
| PVP K30 | 2% w/v |
| Ethanol | 10% v/v |
| N-Methyl Pyrrolidone | 34% v/v |
| Neotame | 0.01% w/w |
| Propylene glycol | q.s to 100% |
| pH | 7.9 |

Formulation 17:

| Ingredients | Quantity in Percentage (%) |
|---|---|
| Zolpidem tartrate | 2.5% w/v |
| Meglumine | 1.4% w/v |
| PVP K30 | 2% w/v |
| Ethanol | 10% v/v |
| Ethyl acetate | 20% v/v |
| Neotame | 0.01% w/w |
| Propylene glycol | q.s to 100% |
| pH | 7.7 |

Formulation 18:

| Ingredients | Quantity in Percentage (%) |
|---|---|
| Zolpidem tartrate | 2.5% w/v |
| Meglumine | 1.4% w/v |
| PVP K30 | 2% w/v |
| Ethanol | 10% v/v |
| DiMethylIsosorbide | 24% v/v |
| Neotame | 0.01% w/w |
| Propylene glycol | q.s to 100% |
| pH | 7.5 |

Formulation 19:

| Ingredients | Quantity in Percentage (%) |
|---|---|
| Zolpidem tartrate | 2.5% w/v |
| Meglumine | 1.4% w/v |
| PVP K30 | 2% w/v |
| Ethanol | 10% v/v |
| Dimethyl Acetamide | 30% v/v |
| Neotame | 0.01% w/w |
| Propylene glycol | q.s to 100% |
| pH | 7.9 |

Formulation 20:

| Ingredients | Quantity in Percentage (%) |
|---|---|
| Zolpidem tartrate | 2.5% w/v |
| Meglumine | 1.4% w/v |
| PVP K30 | 2% w/v |
| Ethanol | 10% v/v |
| Benzyl Alcohol | 40% v/v |

-continued

| Ingredients | Quantity in Percentage (%) |
|---|---|
| Neotame | 0.01% w/w |
| Propylene glycol | q.s to 100% |
| pH | 7.6 |

Formulation 21:

| Ingredients | Quantity in Percentage (%) |
|---|---|
| Zolpidem tartrate | 4% w/v |
| Meglumine | 2.24% w/v |
| PVP K30 | 2% w/v |
| Ethanol | 20% v/v |
| Glycerol | 20% v/v |
| Propylene glycol | q.s to 100% |
| pH | 8.0 |

Formulation 22:

| Ingredients | Quantity in Percentage (%) |
|---|---|
| Zolpidem tartrate | 1.25% w/v |
| Ethanol | 20% v/v |
| Glycerol | 40% v/v |
| Propylene glycol | q.s to 100% |
| pH | 5.6 |

Formulation 23:

| Ingredients | Quantity in Percentage (%) |
|---|---|
| Zolpidem tartrate | 1.25% w/v |
| Sodium lauryl Sulfate (SLS) | 2% w/v |
| Glycerol | 20% v/v |
| Propylene glycol | q.s to 100% |
| pH | 5.3 |

Formulation 24:

| Ingredients | Quantity in Percentage (%) |
|---|---|
| Zolpidem tartrate | 2.5% w/v |
| Ethanol | 10% v/v |
| Glycerol | 25% v/v |
| Propylene glycol | q.s to 100% |
| pH | 5.2 |

Auxiliary ingredients such as sweetener, flavoring agent, taste masking agents etc may be added in the formulation.

All the solutions prepared in accordance with the present invention were in the form of clear solutions and were found to be stable throughout their shelf-life. The stable non-aqueous solutions of the present invention are suitable for administration by oromucosal route (across oral mucosa).

Without limiting to any particular process or sequence of addition of ingredients, the solutions of the present invention are prepared using the processes known in the art.

Comparative Pharmacokinetic Study:

The examples disclosed above are representative of the formulations covered in the present invention. The scope of the present invention is not limited to any of these examples. The advantageous features provided by these representative formulations of the present invention are also provided by all the formulations covered in the scope of the present invention.

A cross-over comparative pharmacokinetic study of the formulations of the present invention (Formulations 1 & 2) with those of the formulations available in the market (Comparative Formulation 3—Zolpimist) was carried out following single dose administration in male New Zealand white rabbits to compare the pharmacokinetics of Zolpidem following buccal or sublingual administration. A dose equivalent to 10 mg of human dose (0.52 mg/kg by wt) was administered to rabbits by buccal or sublingual route. Sampling was carried out at different time points such as pre-dose, 5 min, 10 min, 20 min, 30 min, 45 min, 1 hr, 2 hr & 3 hr post dosing in each study period. The plasma samples were analyzed for quantification of Zolpidem using a validated LC-MS/MS method. Pharmacokinetic analysis was carried out using the non-compartmental analysis tool of the validated Phoenix WinNonlin® software and the values of $T_{max}$, $C_{max}$ and $AUC_{0-3\ hr}$ were obtained. The statistical analysis was carried out by ANOVA method at $p<0.05$ using SAS® software.

Results: Among all the formulations tested, Formulation 1 provided the shortest $T_{max}$ of about 5 minutes. The difference between the $T_{max}$ of Formulations 1 and 2 was found to be statistically insignificant. The comparative Formulation 3 resulted in the $T_{max}$ of 20 minutes. The difference between the $T_{max}$ of the Formulation 1 and 2 with comparative Formulation 3 was found to be statistically significant. No significant difference was observed in the values of $C_{max}$ and $AUC_{0-3\ hr}$ between the formulations tested.

Prior-art formulations fail to provide a higher concentration of drug in stable, non-aqueous liquid dosage form and at the same time use minimised proportion of penetration enhancer and yet achieve enhanced transmucosal penetration of the drug.

In contrast, the present formulation provides stable, liquid, dosage form of Zolpidem or its pharmaceutically acceptable salts wherein the drug not only remains in completely solubilized state, but also remains stable throughout the shelf life of the solutions and achieves rapid transmucosal penetration of the drug. The non-aqueous liquid solutions of the present invention not only provide a stable solutions with desirable drug concentration but surprisingly result in significantly rapid onset of action due to quicker transmucosal penetration of the drug. Surprisingly, the present invention provides the above advantage by minimizing the amount of penetration enhancer(s) in the solutions.

The present invention has surprisingly found that stable, non-aqueous solutions of Zolpidem comprising 0.5 to 10% w/v of Zolpidem or Pharmaceutically acceptable salts thereof, a penetration enhancer and a non-aqueous solvent in the pH range of 5 to 9 provides enhanced transmucosal penetration leading to fast onset of action. Preferably the pH of the solutions of the present invention is in the range of 6 to 9, more preferably the pH of the solutions of the present invention is in the range of 7 to 9.

We claim:

1. A stable oromucosal solution of zolpidem or its pharmaceutically acceptable salt thereof comprising:
   0.5% to 10% w/v of zolpidem or its pharmaceutically acceptable salt thereof,
   2% to 30% v/v of a penetration enhancer selected from any one or more of a lower straight-chain alcohol with a carbon length of 1 to 5, sodium glycocholate, sodium deoxycholate, sodium taurocholate, sodium glycodeoxycholate, sodium taurodeoxycholate, oleic acid, capric acid, lauric acid, lecithin, myristic acid, palmitic acid, lysophosphatidylcholine, phosphatidylcholine, azone, cyclodextrin, sodium lauryl sulphate, polyoxyethylene-9-laurylether, polyoxythylene-20-cetylether, benzalkonium chloride, cetylpyridinium chloride, vitamin E TPGS, caprylocaproyl polyoxylglycerides, stearoyl macrogolglycerides or propylene glycol dicaprylocaprate, and 40% to 99.5% v/v of a non-aqueous polar solvent selected from any one or more of glycerol, propylene glycol, polyethylene glycol, propylene carbonate, glycofurol, isopropyl myristate, isopropyl palmitate, dimethyl sulfoxide, triethyl citrate, dimethyl acetamide, benzyl alcohol, N-methyl-pyrrolidone, dimethyl isosorbide or ethyl acetate, wherein the pH of the oromucosal solution is 5 to 9, and wherein the oromucosal solution is devoid of added water.

2. The stable oromucosal solution as claimed in claim 1, wherein the solution comprises 2.5% to 10% w/v of zolpidem or its pharmaceutically acceptable salt thereof.

3. The stable oromucosal solution as claimed in claim 1, wherein the pH of the solution is in the range of 6 to 9.

4. The stable oromucosal solution as claimed in claim 1, wherein the lower straight-chain alcohol is any one or more of ethanol or isopropyl alcohol.

5. The stable oromucosal solution as claimed in claim 1, wherein the penetration enhancer is in the range of 10% to 30% v/v of the solution.

6. The stable oromucosal solution as claimed in claim 1, wherein the penetration enhancer is in the range of 2% to 25% v/v of the solution.

7. A stable oromucosal solution of zolpidem or its pharmaceutically acceptable salts thereof comprising:

2.5% to 10% w/v of zolpidem or its pharmaceutically acceptable salt thereof,

2% to 30% v/v of a penetration enhancer selected from any one or more of a lower straight-chain alcohol with a carbon length of 1 to 5, sodium glycocholate, sodium deoxycholate, sodium taurocholate, sodium glycodeoxycholate, sodium taurodeoxycholate, oleic acid, capric acid, lauric acid, lecithin, myristic acid, palmitic acid, lysophosphatidylcholine, phosphatidylcholine, azone, cyclodextrin, sodium lauryl sulphate, polyoxyethylene-9-laurylether, polyoxythylene-20-cetylether, benzalkonium chloride, cetylpyridinium chloride, vitamin E TPGS, caprylocaproyl polyoxylglycerides, stearoyl macrogolglycerides or propylene glycol dicaprylocaprate, 40% to 99.5% v/v of a non-aqueous polar solvent selected from any one or more of glycerol, propylene glycol, polyethylene glycol, propylene carbonate, glycofurol, isopropyl myristate, isopropyl palmitate, dimethyl sulfoxide, triethyl citrate, dimethyl acetamide, benzyl alcohol, N-methyl-pyrrolidone, dimethyl isosorbide or ethyl acetate, a pH adjusting agent, and a polymer selected from any one or more of poly vinylpyrrolidone, poly(vinyl pyrrolidone-co-vinyl acetate), polyvinylpolypyrrolidone, polymethacrylates, hydroxypropylmethyl cellulose, hydroxypropylmethyl cellulose acetate succinate, hydroxyethyl cellulose, hydroxypropyl cellulose, hydroxypropyl betadex, polyvinyl alcohol, polyacrylic acid or mixtures thereof, wherein the pH of the oromucosal solution is 5 to 9, and wherein the oromucosal solution is devoid of added water.

8. The stable oromucosal solution as claimed in claim 7, wherein the solution comprises up to 5% w/v of the polymer.

9. The stable oromucosal solution as claimed in claim 7, wherein the solution comprises 1 to 2.8% v/v of the pH adjusting agent.

10. The stable oromucosal solution as claimed in claim 7, wherein the pH adjusting agent is selected from any one or more of meglumine, triethanolamine, tromethamine, diethanolamine, monoethanolamine or combination thereof.

11. A stable oromucosal solution of zolpidem or its pharmaceutically acceptable salt thereof comprising:

2.5% to 10% w/v of zolpidem or its pharmaceutically acceptable salt thereof,

2% to 30% v/v of a penetration enhancer selected from any one or more of a lower straight-chain alcohol with a carbon length of 1 to 5, sodium glycocholate, sodium deoxycholate, sodium taurocholate, sodium glycodeoxycholate, sodium taurodeoxycholate, oleic acid, capric acid, lauric acid, lecithin, myristic acid, palmitic acid, lysophosphatidylcholine, phosphatidylcholine, azone, cyclodextrin, sodium lauryl sulphate, polyoxyethylene-9-laurylether, polyoxythylene-20-cetylether, benzalkonium chloride, cetylpyridinium chloride, vitamin E TPGS, caprylocaproyl polyoxylglycerides, stearoyl macrogolglycerides or propylene glycol dicaprylocaprate, 40% to 99.5% v/v of a non-aqueous polar solvent selected from any one or more of glycerol, propylene glycol, polyethylene glycol, propylene carbonate, glycofurol, isopropyl myristate, isopropyl palmitate, dimethyl sulfoxide, triethyl citrate, dimethyl acetamide, benzyl alcohol, N-methyl-pyrrolidone, dimethyl isosorbide or ethyl acetate, and a pH adjusting agent, wherein the pH of the oromucosal solution is 5 to 9, and wherein the oromucosal solution is devoid of added water.

12. The stable oromucosal solution as claimed in claim 11, wherein the solution comprises 1 to 2.8% v/v of the pH adjusting agent.

13. The stable oromucosal solution as claimed in claim 11, wherein the pH adjusting agent is selected from any one or more of meglumine, triethanolamine, tromethamine, diethanolamine, monoethanolamine or combination thereof.

* * * * *